United States Patent [19]

O'Callaghan et al.

[11] Patent Number: 4,504,477
[45] Date of Patent: Mar. 12, 1985

[54] CEPHALOSPORIN ANTIBIOTICS

[75] Inventors: Cynthia H. O'Callaghan, Gerrards Cross; Barry E. Ayres, Ickenham; David G. H. Livermore, Princes Risborough; Christopher E. Newall, London; Niall G. Weir, Wembley, all of England

[73] Assignee: Glaxo Group Limited, London, England

[21] Appl. No.: 285,492

[22] Filed: Jul. 21, 1981

Related U.S. Application Data

[63] Continuation of Ser. No. 176,536, Aug. 8, 1980, abandoned, which is a continuation of Ser. No. 095,062, Nov. 16, 1979, abandoned.

[30] Foreign Application Priority Data

Nov. 17, 1978 [GB] United Kingdom ............... 44873/78

[51] Int. Cl.$^3$ ............... C07D 501/36; A61K 31/545
[52] U.S. Cl. ........................... 514/203; 544/24; 544/25; 544/26
[58] Field of Search ............ 424/246; 544/25, 26, 544/27

[56] References Cited

U.S. PATENT DOCUMENTS 4,144,392  3/1979  Bradshaw et al. .................. 544/29
4,237,128  12/1980 Cimarusti et al. .................. 544/25
4,278,793  7/1981  Durckheimer et al. ............. 544/25
4,315,005  2/1982  Ayas et al. ........................... 544/25
4,394,503  7/1983  Kamachi et al. .................... 544/25

Primary Examiner—Nicholas S. Rizzo
Attorney, Agent, or Firm—Bacon & Thomas

[57] ABSTRACT

Cephalosporin antibiotics of general formula

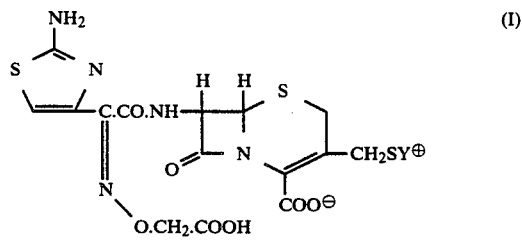

(I)

(wherein $Y^\oplus$ represents a C-attached 1-$C_{1-4}$alkyl-pyridinium group) exhibit broad spectrum antibiotic activity with unusually high activity against strains of Pseudomonas organisms as well as high activity against various members of the Enterobacteriaceae. The invention also includes the non-toxic salts, non-toxic metabolically labile esters and 1-oxides of compounds of formula (I). Also described are compositions containing the antibiotics of the invention and processes for the preparation of the antibiotics.

10 Claims, No Drawings

CEPHALOSPORIN ANTIBIOTICS

This application is a continuation, of application Ser. No. 176,536, filed 08/08/80, now abandoned which is a continuation of Ser. No. 095,062, filed 11/16/79, now abandoned.

The cephalosporin compounds in this specification are named with reference to "cepham" after *J. Amer. Chem. Soc.*, 1962, 84, 3400, the term "cephem" referring to the basic cepham structure with one double bond.

The present invention provides cephalosporin antibiotics of the general formula:

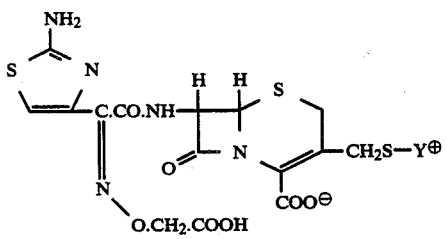

(wherein $Y^\oplus$ represents a C-attached 1-$C_{1-4}$ alkyl-pyridinium group) and non-toxic salts, non-toxic metabolically labile esters and 1-oxides (preferably the 1S-oxide) thereof.

It will be appreciated that the group $Y^\oplus$ may be attached to the sulphur atom at the 2-, 3- or 4-position of the pyridine ring.

The compounds according to the invention are syn isomers. The syn isomeric form is defined by the configuration of the group

—$OCH_2COOH$ with respect to the carboxamido group. In this Specification the syn configuration is denoted structurally as

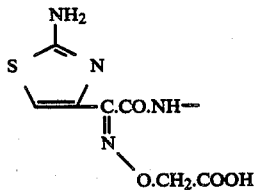

It will be understood that since the compounds according to the invention are geometric isomers, some admixture with the corresponding anti isomer may occur.

The invention also includes within its scope the solvates (especially the hydrates) of the compounds of formula (I). It also includes within its scope salts of esters of compounds of formula (I).

The compounds according to the present invention may exist in tautomeric forms (for example in respect of the 2-aminothiazolyl group) and it will be understood that such tautomeric forms, e.g. the 2-iminothiazolinyl form, are included within the scope of the invention. Moreover, the compounds of formula (I) depicted above may also exist in alternative zwitterionic forms, for example wherein the 4-carboxyl group is protonated and the carboxyl group in the 7-side chain is deprotonated. These alternative forms, as well as mixtures of such zwitterionic forms, are included within the scope of the present invention.

The compounds according to the invention exhibit broad spectrum antibiotic activity against a wide range of commonly encountered pathogenic organisms. Against gram-negative organisms the activity is unusually high. This high activity extends to many β-lactamase-producing gram-negative strains. The compounds also possess high stability to β-lactamases produced by a range of gram-negative and gram-positive organisms.

Compounds according to the invention have been found to exhibit unusually high activity against strains of Pseudomonas organisms, e.g. strains of *Pseudomonas aeruginosa* as well as high activity against various members of the Enterobacteriaceae (e.g. strains of *Escherichia coli, Klebsiella pneumoniae, Salmonella typhimurium, Shigella sonnei, Enterobacter cloacae, Serratia marcescens*, Providencia species, *Proteus mirabilis*, and especially indole-positive Proteus organisms such as *Proteus vulgaris* and *Proteus morganii*) and strains of *Haemophilus influenzae*.

The antibiotic properties of the compounds according to the invention compare very favourably with those of the aminoglycosides such as amikacin or gentamicin. In particular, this applies to their activity against strains of various Pseudomonas organisms which are not susceptible to the many of the existing commercially available antibiotic compounds. Unlike the aminoglycosides, cephalosporin antibiotics normally exhibit low toxicity in man. The use of aminoglycosides in human therapy tends to be limited or complicated by the relatively high toxicity of these antibiotics. The cephalosporin antibiotics of the present invention thus possess potentially great advantages over the aminoglycosides.

Non-toxic salt derivatives which may be formed by reaction of either or both of the carboxyl groups present in the compounds of general formula (I) include inorganic base salts such as alkali metal salts (e.g. sodium and potassium salts) and alkaline earth metal salts (e.g. calcium salts); amino acid salts (e.g. lysine and arginine salts); organic base salts (e.g. procaine, phenethylbenzylamine, dibenzylethylenediamine, ethanolamine, diethanolamine and N-methylglucosamine salts). Other non-toxic salt derivatives include acid addition salts, e.g. formed with hydrochloric, hydrobromic, sulphuric, nitric, phosphoric, formic and trifluoroacetic acids. The salts may also be in the form of resinates formed with, for example, a polystyrene resin or cross-linked polystyrene divinylbenzene copolymer resin containing amino or quaternary amino groups or sulphonic acid groups, or with a resin containing carboxyl groups, e.g. polyacrylic acid resin. Soluble base salts (e.g. alkali metal salts such as the sodium salt) of compounds of formula (I) may be used in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

These and other salt derivatives such as the salts with toluene-p-sulphonic and methanesulphonic acids may be employed as intermediates in the preparation and/or purification of the present compounds of formula (I), for example in the processes described below.

Non-toxic metabolically labile ester derivatives which may be formed by esterification of either or both carboxyl groups in the parent compound of formula (I)

include acyloxyalkyl esters e.g. lower alkanoyloxymethyl or -ethyl esters such as acetoxy-methyl or -ethyl or pivaloyloxymethyl esters. In addition to the above ester derivatives, the present invention includes within its scope compounds of formula (I) in the form of other physiologically acceptable equivalents, i.e. physiologically acceptable compounds which, like the metabolically labile esters are converted in vivo into the parent antibiotic compound of formula (I).

Preferred compounds according to the present invention include those compounds of formula (I) wherein the $C_{1-4}$ alkyl substituent in the group $Y^\oplus$ is a methyl group. Preference is also expressed for those compounds wherein the group $Y^\oplus$ is attached to the sulphur atom at the 2- or 4-position of the pyridine ring.

Particularly preferred compounds according to the invention therefore include the following compounds of formula (I) and their non-toxic salts and non-toxic metabolically labile esters: (6R,7R)-7-[(Z)-2-(2-aminothiazol-4-yl)-2-(carboxymethoxyimino)acetamido]-3-(1-methylpyridinium-2-ylthiomethyl)ceph-3-em-4-carboxylate; and (6R,7R)-7-[(Z)-2-(2-aminothiazol-4-yl)-2-(carboxymethoxyimino)acetamido]-3-(1-methylpyridinium-4-ylthiomethyl)-ceph-3-em-4-carboxylate.

Other compounds according to the present invention include the 3-(1-methylpyridinium-3-ylthiomethyl) analogue of the above two compounds as well as the three corresponding compounds in which the N-substituent on the pyridinium ring is an ethyl group.

The compounds of formula (I) may be used for treating a variety of diseases caused by pathogenic bacteria in human beings and animals, such as respiratory tract infections and urinary tract infections.

According to another embodiment of the invention we provide a process for the preparation of an antibiotic compound of general formula (I) as hereinbefore defined or a non-toxic salt, non-toxic metabolically labile ester or 1-oxide thereof which comprises (A) acylating a compound of the formula

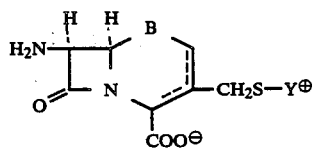

[wherein $Y^\oplus$ is as defined above; B is S or >S→O (α- or β-); and the dotted line bridging the 2-, 3- and 4-positions indicates that the compound is a ceph-2-em for ceph-3-em compound] or a salt, e.g. an acid addition salt (formed with, for example, a mineral acid such as hydrochloric, hydrobromic, sulphuric, nitric or phosphoric acid or an organic acid such as methanesulphonic or toluene-p-sulphonic acid) or an N-silyl derivative thereof, or a corresponding compound having a group of formula-$COOR^1$ at the 4-position [where $R^1$ is a hydrogen atom or a carboxyl blocking group, e.g. the residue of an ester-forming aliphatic or araliphatic alcohol or an ester-forming phenol, silanol or stannanol (the said alcohol, phenol, silanol or stannanol preferably containing 1–20 carbon atoms)] and having an associated anion $A^\ominus$ such as a halide, e.g. chloride or bromide, or trifluoroacetate anion, with an acid of formula

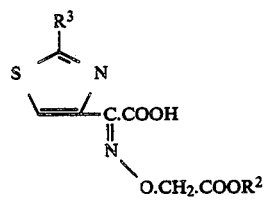

(wherein $R^2$ represents a carboxyl blocking group, e.g. as described for $R^1$; and $R^3$ is an amino or protected amino group) or with an acylating agent corresponding thereto; (B) reacting a compound of formula

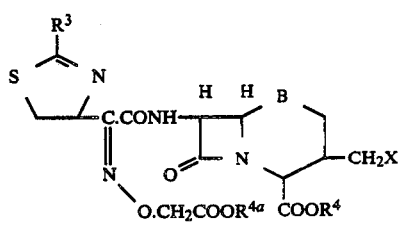

(wherein $R^3$, B and the dotted line are as hereinbefore defined; $R^4$ and $R^{4a}$ may independently represent hydrogen or a carboxyl blocking group; and X is a replaceable residue of a nucleophile, e.g. an acetoxy or dichloroacetoxy group or a halogen atom such as chlorine, bromine or iodine) or a salt thereof with a sulphur nucleophile serving to form the group —$CH_2$—S—$Y^\oplus$ wherein $Y^\oplus$ is as defined above) at the 3-position; or (C) alkylating a compound of formula

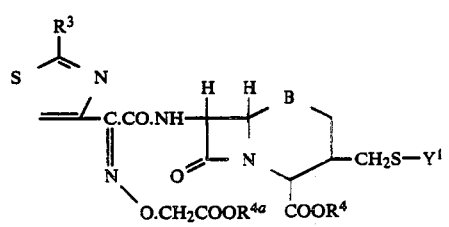

(wherein $R^3$, B and the dotted lines are as hereinbefore defined; $Y^1$ is a C-attached pyridyl group; and $R^4$ and $R^{4a}$ in this instance are both carboxyl blocking groups) with a $C_{1-4}$ alkylating agent serving to introduce a $C_{1-4}$ alkyl group as a substituent on the nitrogen atom of the pyridine ring; whereafter, if necessary and/or desired in each instance, any of the following reactions (D) in any appropriate sequence, are carried out:

(i) conversion of a $\Delta^2$-isomer into the desired $\Delta^3$-isomer,
(ii) reduction of a compound wherein B is >S→O to form a compound wherein B is >S,
(iii) conversion of a carboxyl group into a non-toxic salt or non-toxic metabolically labile ester function,
(iv) oxidation of a compound wherein B is >S to form a compound wherein B is >S→O, and
(v) removal of any carboxyl blocking and/or N-protecting groups.

In the above-described processes, the cephalosporin starting materials are preferably compounds wherein the dotted line represents ceph-3-em compounds.

The reaction should be effected in the presence of a base if an acid addition salt of the compound of formula (II) is used.

Acylating agents which may be employed in the preparation of compounds of formula (I) include acid halides, particularly acid chlorides or bromides. Such acylating agents may be prepared by reacting an acid (III) or a salt thereof with a haolgenating agent e.g. phosphorus pentachloride, thionyl chloride or oxalyl chloride.

Acylations employing acid halides may be effected in aqueous and non-aqueous reaction media, conveniently at temperatures of from $-50°$ to $+50°$ C., preferably $-20°$ to $+30°$ C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (III) may themselves be used as acylating agents in the preparation of compounds of formula (I). Acylations employing acids (III) are desirably conducted in the presence of a condensing agent, for example a carbodiimide such as N,N'-dicyclohexylcarbodiimide or N-ethyl-N'-γ-dimethylaminopropylcarbodiimide; a carbonyl compound such as carbonyldiimidazole; or an isoxazolium salt such as N-ethyl-5-phenylisoxazolium perchlorate.

Acylation may also be effected with other amide-forming derivatives of acids of formula (III) such as, for example, an activated ester, a symmetrical anhydride or a mixed anhydride (e.g. formed with pivalic acid or with a haloformate, such as a lower alkylhaloformate). Mixed anhydrides may also be formed with phosphorus acids (for example phosphoric or phosphorous acids), sulphuric acid or aliphatic or aromatic sulphonic acids (for example toluene-p-sulphonic acid). An activated ester may conveniently be formed in situ using, for example, 1-hydroxy-benzotriazole in the presence of a condensing agent as set out above. Alternatively, the activated ester may be preformed.

Acylation reactions involving the free acids or their above-mentioned amide-forming derivatives are desirably effected in an anhydrous reaction medium, e.g. methylene chloride, tetrahydrofuran, dimethylformamide acetonitrile.

If desired, the above acylation reactions may be carried out in the presence of a catalyst such as 4-dimethylaminopyridine.

The acids of formula (III) and acylating agents corresponding thereto may, if desired, be prepared and employed in the form of their acid addition salts. Thus, for example, acid chlorides may conveniently be employed as their hydrochloride salts, and acid bromides as their hydrobromide salts.

In process (B) the sulphur nucleophile may serve to displace a wide variety of substituents X from the cephalosporin of formula (IV). To some extent the facility of the displacement is related to the $pK_a$ of the acid HX from which the substituent is derived. Thus atoms or groups X derived from strong acids tend, in general, to be more easily displaced than atoms or groups derived from weaker acids. The facility of the displacement is also related, to some extent, to the precise identity of the sulphur nucleophile. The latter nucleophile may be employed for example in the form of the appropriate thione or thiolate.

The displacement of X by the sulphur nucleophile may conveniently be effected by maintaining the reactants in solution or suspension. The reaction is advantageously effected using from 1 to 10, preferably 1 to 4, mole equivalents of the nucleophile.

Nucleophilic displacement reactions may conveniently be carried out on those compounds of formula (IV) wherein the substituent X is a halogen atom or an acyloxy group for example as discussed below.

Acyloxy groups

Compounds of formula (IV) wherein X is an acetoxy group are convenient starting materials for use in the nucleophilic displacement reaction with the sulphur nucleophile. Alternative starting materials in this class include compounds of formula (IV) in which X is the residue of a substituted acetic acid e.g. chloroacetic acid, dichloroacetic acid and trifluoroacetic acid.

Displacement reactions on compounds (IV) possessing X substituents of this class, particularly in the case where X is an acetoxy group, may be facilitated by the presence in the reaction medium of iodide or thiocyanate ions.

The substituent X may also be derived from formic acid, a haloformic acid such as chloroformic acid, or a carbamic acid.

When using a compound of formula (IV) in which X represents an acetoxy or substituted acetoxy group, it is generally desirable that the group $R^4$ in formula (IV) should be a hydrogen atom and that B should represent $>S$. In this case, the reaction is advantageously effected in an aqueous medium, preferably at a pH of 5 to 8, particularly 5.5 to 7. These pH ranges may be achieved, if necessary by the addition of a base for example an alkali metal or alkaline earth metal hydroxide or bicarbonate such as sodium hydroxide or bicarbonate. A base is generally used when the compound of formula (IV) is in the form of an acid addition salt.

The above-described process employing compounds of formula (IV) in which X is the residue of a substituted acetic acid may be carried out as described in British Patent Specification No. 1,241,657.

When using compounds of formula (IV) in which X is an acetoxy group, the reaction is conveniently effected at a temperature of 30° to 110°, preferably 50° to 80° C.

Halogens

Compounds of formula (IV) in which X is a chlorine, bromine or iodine atom can also be conveniently used as starting materials in the nucleophilic displacement reaction with the sulphur nucleophile. When using compounds of formula (IV) in this class, B may represent $>S \rightarrow O$ and $R^4$ may represent a carboxyl blocking group. The reaction is conveniently effected in a nonaqueous medium which preferably comprises one or more organic solvents, advantageously of a polar nature, such as ethers, e.g. dioxan or tetrahydrofuran, esters, e.g. ethyl acetate, amides, e.g. formamide or N,N-dimethylformamide, or ketones, e.g. acetone. Other suitable organic solvents are described in more detail in British Patent Specification No. 1,326,531. The reaction medium should be neither extremely acidic nor extremely basic. In the case of reactions carried out on compounds of formula (IV) in which $R^4$ and $R^{4a}$ are carboxyl blocking groups the 3-(1-methyl-pyridinium)-thiomethyl product will be formed as the corresponding halide salt which may, if desired, be subjected to one or more ion exchange reactions to obtain a salt having the desired anion.

When using compounds of formula (IV) in which X is a halogen atom as described above, the reaction is conveniently effected at a temperature of $-20°$ to $+50°$ C., preferably $0°$ to $+30°$ C.

In process (C) above, the compound of formula (V) is advantageously reacted with a $C_{1-4}$ alkylating agent of the formula $R^c Z'$ wherein $R^c$ is a $C_{1-4}$ alkyl group and $Z'$ is a leaving group such as a halogen atom (e.g. iodine, chlorine or bromine) or a hydrocarbylsulphonate (e.g. mesylate or tosylate) group. Alternatively, a di-$(C_{1-4})$ alkylsulphate, e.g. dimethylsulphate, may be employed as the alkylating agent. The alkylation reaction is preferably carried out at a temperature in the range of $0°$ to $60°$ C., advantageously $20°$ to $30°$ C. The reaction may be conveniently effected in an inert solvent such as an ether e.g. tetrahydrofuran, an amide, e.g. dimethylformamide, or a halogenated hydrocarbon, e.g. dichloromethane. Alternatively, where the alkylating agent is liquid under the reaction conditions, this agent can itself serve as a solvent. Iodomethane is a preferred alkylating agent.

The compound of formula (V) used as starting material in process (C) may be prepared for example by reaction of a compound of formula (IV) (as defined above) with an appropriate sulphur nucleophile in an analogous manner to the nucleophilic displacement reaction described with respect to process (B). This reaction is generally carried out in the presence of an acid scavenging agent, e.g. a base as described above in relation to process (B).

The reaction product may be separated from the reaction mixture, which may contain, for example, unchanged cephalosporin starting material and other substances, by a variety of processes including recrystallisation, ionophoresis, column chromatography and use of ion-exchangers (for example by chromatography on ion-exchange resins) or macroreticular resins.

A $\Delta^2$-cephalosporin ester derivative obtained in accordance with the process of the invention may be converted into the corresponding $\Delta^3$-derivative by, for example, treatment of the $\Delta^2$-ester with a base such as pyridine or triethylamine.

A ceph-2-em reaction product may also be oxidised to yield the corresponding ceph-3-em 1-oxide, for example by reaction with a peracid, e.g. peracetic or m-chloroperbenzoic acid; the resulting sulphoxide may, if desired, subsequently be reduced as described hereinafter to yield the corresponding ceph-3-em sulphide.

Where a compound is obtained in which B is S→O this may be converted to the corresponding sulphide by, for example, reduction of the corresponding acyloxysulphonium or alkoxysulphonium salt prepared in situ by reaction with e.g. acetyl chloride in the case of an acetoxysulphonium salt, reduction being effected by, for example, sodium dithionite or by iodide ion as in a solution of potassium iodide in a water-miscible solvent e.g. acetic acid, acetone, tetrahydrofuran, dioxan, dimethylformamide or dimethylacetamide. The reaction may be effected at a temperature of from $-20°$ to $+50°$ C.

Metabolically labile ester derivatives of the compounds of formula (I) may be prepared by reacting a compound of formula (I) or a salt or protected derivative thereof with an appropriate esterifying agent such as an acyloxyalkyl halide (e.g. iodide) conveniently in an inert organic solvent such as dimethylformamide or acetone, followed, where necessary, by removal of any protecting groups.

Base salts of the compounds of formula (I) may be formed by reacting an acid of formula (I) with the appropriate base. Thus, for example, sodium or potassium salts may be prepared using the respective 2-ethylhexanoate or hydrogen carbonate salt. Acid addition salts may be prepared by reacting a compound of formula (I) or a metabolically labile ester derivative thereof with the appropriate acid.

1-oxides may be prepared by oxidation of the corresponding 1-sulphide, e.g. with a per acid.

Where a compound of formula (I) is obtained as a mixture of isomers, the syn isomer may be obtained by, for example, conventional methods such as crystallisation or chromatography.

For use as starting materials for the preparation of compounds of general formula (I) according to the invention, compounds of general formula (III) and acid halides and anhydrides corresponding thereto in their syn isomeric form or in the form of mixtures of the syn isomers and the corresponding anti isomers containing at least 90% of the syn isomer are preferably used.

The acids of formula (III) and the compounds of formula (IV) wherein X represents an acetoxy group may be prepared by the methods described in South African Patent Specification No. 78/1630.

Where X is a halogen (i.e. chlorine, bromine or iodine) atom in formula (IV), ceph-B 3-em starting compounds may be prepared in conventional manner, e.g. by halogenation of a 7β-protected amino-3-methylceph-3-em-4-carboxylic acid ester 1β-oxide, removal of the 7β-protecting group, acylation of the resulting 7β-amino compound to form the desired 7β-acylamido group, e.g. in an analogous manner to process (A) above, followed by redution of the 1β-oxide group later in the sequence. This is described in British Patent No. 1,326,531. The corresponding ceph-2-em compounds may be prepared by the method of Dutch published Patent Application No. 6,902,013 by reaction of a 3-methylceph-2-em compound with N-bromosuccinimide to yield the corresponding 3-bromomethylceph-2-em compound.

Compounds of formula (IV) in which X represents acyloxy groups other than acetoxy can be prepared by acylation of the corresponding 3-hydroxymethyl compounds which may be prepared for example by hydrolysis of the appropriate 3-acetoxymethyl compounds, e.g. as described in British Patent Specifications Nos. 1,474,519 and 1,531,212.

The starting materials of formula (II) may be prepared in conventional manner, for example, by nucleophilic displacement of the corresponding 3-acetoxymethyl compound with the appropriate nucleophile.

A further method for the preparation of the starting materials of formula (II) comprises deprotecting a corresponding protected 7β-amino compound in conventional manner e.g. using $PCl_5$.

It should be appreciated that in some of the above transformations it may be necessary to protect any sensitive groups in the molecule of the compound in question to avoid undesirable side reactions. For example, during any of the reaction sequences referred to above it may be necessary to protect the $NH_2$ group of the aminothiazolyl moiety, for example by tritylation, acylation (e.g. chloroacetylation), protonation or other conventional method. The protecting group may thereafter be removed in any convenient way which does not cause breakdown of the desired compound, e.g. in the case of a trityl group by using an optionally halogenated carboxylic acid, e.g. acetic acid, formic acid, chloroacetic acid or trifluoroacetic acid or using a mineral acid, e.g. hydrochloric acid or mixtures of such acids, preferably in the presence of a protic solvent such as water or, in the case of a chloroacetyl group, by treatment with thiourea.

Carboxyl blocking groups used in the preparation of compounds of formula (I) or in the preparation of necessary starting materials are desirably groups which may readily be split off at a suitable stage in the reaction sequence, conveniently at the last stage. It may, however, be convenient in some instances to employ nontoxic metabolically labile carboxyl blocking groups such as acyloxy-methyl or -ethyl groups (e.g. acetoxymethyl or-ethyl or pivaloyloxymethyl) and retain these in the final product to give an appropriate ester derivative of a compound of formula (I).

Suitable carboxyl blocking groups are well known in the art, a list of representative blocked carboxyl groups being included in British Pat. No. 1,399,086. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. Carboxyl blocking group(s) may subsequently be removed by any of the appropriate methods disclosed in the literature; thus, for example, acid or base catalysed hydrolysis is applicable in many cases, as are enzymically-catalysed hydrolyses.

The following Examples illustrate the invention. All temperatures are in °C.

Proton magnetic resonance (p.m.r.) spectra are inserted where appropriate and were determined at 100 MHz. The integrals are in agreement with the assignments, and the signs of the coupling constants, were not determined; s=singlet, d=doublet and m=multiplet.

EXAMPLE 1

(6R,7R)-7-[(Z)-2-(2-Aminothiazol-4-yl)-2-(carboxymethoxyimino)acetamido]-3-(1-methylpyridinium-2-ylthiomethyl)ceph-3-em-4-carboxylate, sodium salt 1-Methyl pyrid-2-thione (0.6 g) was added to a stirred solution of (6R,7R)-7-[(Z)-2-(2-aminothiazol-4-yl)-2-(carboxymethoxyimino)acetamido]-3-acetoxymethyl-ceph-3-em-4-carboxylic acid disodium salt (1.7 g) (described in Example 5 of South African Specification No. 78/1630) in water (2.1 ml). The pH of the solution was adjusted to about 6.5 with sodium hydrogen carbonate before the addition of sodium iodide (2.9 g). The resulting mixture was stirred and heated, at 65° C., for 5½ hours. When cool, the resulting mixture was added dropwise to acetone (200 ml), giving a solid, which was isolated and washed with diethyl ether and then applied, as a solution in water, to an Amberlite XAD-2 column, which was prepared in water. Elution was by water and aqueous ethanol. Evaporation of a combination of the appropriate fractions gave, after trituration with diethyl ether, the title compound as a solid (0.7 g), $\lambda_{max}$ (pH 6 buffer) 243 mn ($E_1\ _{cm}^{1\%}$ 321), $\lambda_{max}$ 308 nm ($E_1\ _{cm}^{1\%}$ 203); $\nu_{max}$ (Nujol) 2500–3700 (—NH,—NH$_2$), 1770 (β-lactam), 1670, 1540 (7-CONH), 1610 cm$^{-1}$ (—CO$_2^\ominus$).

EXAMPLE 2

(a) Diphenylmethyl (6R,7R)-3-Bromomethyl-7-[(Z)-2-(t-butoxycarbonylmethoxyimino)-2-(2-tritylaminothiazol-4-yl)acetamido]ceph-3-em-4-carboxylate (Z)-2-(t-Butoxycarbonylmethoxyimino)-2-(2-tritylaminothiazol-4-yl)acetic acid (1.1 g) (described in Example 3 of South African Specification No. 78/1630) was added to a stirred solution of phosphorus pentachloride (0.46 g) in dichloromethane (20 ml) at −20°. The solution was kept at −15°±5° for 40 35 minutes. More phosphorus pentachloride (0.05 g) was added after 30 minutes. The solution was cooled to −20° and triethylamine (0.6 ml) was added. The solution was stirred at −20° for 5 minutes and then added to a stirred solution of diphenylmethyl (6R,7R)-7-amino-3-bromomethylceph-3-em-4-carboxylate, hydrochloride salt (1 g) in dichloromethane (20 ml) containing triethylamine (0.3 ml) at −20°. The temperature did not exceed −20° during the addition. The mixture was stirred at −20° for 10 minutes and then warmed to 22° over 45 minutes. The mixture was diluted with water (25 ml) and dichloromethane (20 ml) and shaken. The organic phase was separated and the aqueous layer was back-washed once with dichloromethane. The organic phase was washed with dilute sodium bicarbonate solution and the aqueous phase was backwashed. The combined organic solutions were washed with dilute brine, dried over sodium sulphate, and evaporated to a foam. This was triturated with diisopropyl ether, filtered, and dried in vacuo at 60° for 2 hours followed by room temperature overnight to give the title compound, (1.7 g), $[\alpha]_D^{21}$ −28° (c 1.0 CHCl$_3$); $\lambda$inf. (ethanol) 239 nm, $E_1\ _{cm}^{1\%}$ 252; 260 nm, $E_1\ _{cm}^{1\%}$ 196; 265.5 nm, $E_{1cm}^{1\%}$ 193; 273 nm, $E_1\ _{cm}^{1\%}$ 181.

(b) Diphenylmethyl (6R,7R)-7-[(Z)-2-(t-Butoxycarbonylmethoxyimino)-2-(2-tritylaminothiazol-4-yl)acetamido]-3-(1p-methylpyridinium-4-ylthiomethyl)ceph-3-em-4-carboxylate bromide A mixture of the product of stage (a) (1.48 g) and N-methylpyrid-4-thione (0.19 g) in tetrahydrofuran (15 ml) was stirred at 22° for 3 hours and then stood at 5° for 18 hours. The mixture was diluted with ether (60 ml) with stirring, cooled to 0° and then filtered. The solid was washed with ether, collected, and dried in vacuo at 60° for 1 hour to give the title compound (1.5 g), $[\alpha]_D^{21}$ −56° (c 1.0, CHCl$_3$); $\lambda_{max}$. (ethanol) 306.5 nm, $E_1\ _{cm}^{1\%}$ 230; $\lambda_{inf}$ 260, nm, $E_1\ _{cm}^{1\%}$ 173; 235 nm, $E_1\ _{cm}^{1\%}$ 281.

(c) (6R,7R)-7-[(Z)-2-(2-Aminothiazol-4-yl)-2-(carboxymethoxyimino)acetamido]-3-(1-methylpyridinium-4-ylthio methyl)ceph-3-em-4-carboxylate, bishydrochloride salt A solution of the product of stage (b) (1.33 g) in a mixture of trifluoroacetic acid (16 ml) and anisole (5 ml) was stirred at 0° for 1 hour. Water (1.5 ml) was added and the mixture was stirred for 15 minutes and then evaporated. The residue was triturated with ether, and the solid was filtered off and dried. This solid (0.95 g) was dissolved in formic acid (5 ml) and concentrated hydrochloric acid (0.25 ml) was added. The mixture was stirred at 21° for 30 min and then filtered. The solid was washed with a little formic acid. The filtrate and washings were combined and evaporated. The residue was triturated with acetone, and the solid was filtered off, washed with a little acetone and dried in vacuo at 60° for 1 hour to give the title compound as a monoacetone solvate, (0.76 g), $[\alpha]_D^{22}$ −20° (c 0.8, pH 7 buffer); $\lambda_{max}$. (pH 6 buffer) 231.5 nm, $E_{1\ cm}^{1\%}$ 326; 253 nm, $E_{1\ cm}^{1\%}$ 232; 304.5 nm, $E_{1\ cm}^{1\%}$ 378.

EXAMPLE 3

(a) Diphenylmethyl (6R,7R)-7-amino-3-(1-methylpyridinium-4-ylthiomethyl)-ceph-3-em-4-carboxylate bromide Diphenylmethyl (6R,7R)-7-amino-3-bromomethylceph-3-em-4-carboxylate hydrochloride (500 mg) was suspended in tetrahydrofuran (20 ml) and treated with triethylamine (0.14 ml). After stirring for ca 5 minutes at ca 0° the solution was clarified and treated with N-methylpyrid-4-thione (150 mg). The mixture was stirred for 2 hours at ambient temperature, then stored at 0° for 16 hours. The white solid was filtered off, washed with tetrahydrofuran and diethyl ether and dried in vacuo at ambient temperature for 16 hours to yield the title compound (500 mg),τ(DMSO-d$_6$) 1.26 (d, pyridinium protons adjacent to NMe), 2.09 (d,pyridinium protons), 3.01 (s, CH.Ph$_2$), 4.88 (d, J 5 Hz, 7-H), 5.08 (d, J 5 Hz, 6-H), 5.77 (s, 3-CH$_2$ and NMe), 6.15 and 6.50 (m, 2-H$_2$).

(b) Diphenylmethyl (6R,7R)-7p-[(Z)-2-(t-Butoxycarbonylmethoxyimino)-2-(2-tritylaminothiazol-4-yl)acetamido]-3-(1-methylpyridinium-4-ylthiomethyl)ceph-3-em-4-carboxylate halide 2-t-Butoxycarbonylmethoxyimino)-2-(2-tritylaminothiazol-4-yl)acetic acid (0.42 g) was added to a stirred solution of phosphorus pentachloride (0.19 g) in dichloromethane (10 ml) at −10°. The solution was stirred at −10° for 30 minutes, and triethylamine (0.25 ml) was added. The solution was stirred at −5° for 5 minutes and then added to a stirred mixture of the product of stage (a) (0.45 g) in dichloromethane (5 ml) at 0°. The mixture, which dissolved, was warmed to 21°, stirred for 2 hours, and left to stand at 5° for 16 hours. The mixture was partitioned between ethyl acetate and water; the aqueous phase was extracted thoroughly with ethyl acetate. The combined organic phase was washed with brine, dried over sodium sulphate and evaporated. The residue was triturated with ether. The solid was collected by filtration and dried in vacuo at 60° to give the title compound (0.55 g), the spectroscopic and chromatographic properties of which resembled those of the product of Example 2(b). The title compound may be deprotected as described in Example 2(c) to yield (6R,7R)-7-[(Z)-2-(2-aminothiazol-4-yl)-2-(carboxymethoxyimino)acetamido]-3-(1-methylpyridinium-4-ylthiomethyl)ceph-3-em-4-carboxylate, bis hydrochloride salt.

EXAMPLE 4

(a) Diphenyl methyl (1S,6R,7R,2′Z)-3-Bromomethyl-7-[2-(butoxycarbonylmethoxyimino)-2-(2-tritylaminothiazol-4-yl)acetamido]ceph-3-em-4-carboxylate, 1-oxide (Z)-2-(t-Butoxycarbonylmethoxyimino)-2-(2-tritylaminothiazol-4-yl)acetic acid (1.63 g) was added to a stirred solution of phosphorus pentachloride (0.69 g) in dichloromethane (25 ml) at −15°. The solution was kept at −15°±5° for 35 minutes. The solution was cooled to −20° and triethylamine (0.9 ml) was added. The solution was stirred at −20° for 5 minutes and then added to a stirred solution of diphenylmethyl (1S,6R,7R)-7-amino-3-bromomethylceph-3-em-4-carboxylate, 1-oxide hydrobromide salt (1.7 g) in dichloromethane (25 ml) containing triethylamine (0.5 ml) at −20°. The temperature did not exceed −15° during the addition. The mixture was stirred at −15° for 10 minutes and then warmed to 21° over 45 minutes. The mixture was diluted with water (40 ml) and dichloromethane (30 ml) and shaken. The organic phase was separated and the aqueous layer was washed with dichloromethane. The organic phase was washed with dilute sodium bicarbonate solution and the aqueous phase was backwashed. The combined organic solutions were washed with dilute brine, dried over sodium sulphate, and evaporated to a foam. This was gradient eluted through a column of kieselgel 60 silica (ca 100 g) with ethyl acetate—60°/80° petroleum ether mixtures. Apropriate fractions were combined and evaporated to foam of the title compound (2.1 g), the spectroscopic and chromatographic properties of which resembled those described below in Example (5a).

(b) Diphenylmethyl (1S,6R,7R)-7-[(Z)-2-(t-Butoxycarbonylmethoxyimino)-2-(2-tritylaminothiazol-4-yl)acetamido]-3-(1-methylpyridinium-4-ylthiomethyl)ceph-3-em-4-carboxylate bromide, 1-oxide A solution of the product of stage (a) (1.9 g) in tetrahydrofuran (20 ml) was treated with N-methylpyrid-4-thione (0.3 g). The mixture, which solidified, was diluted with tetrahydrofuran (30 ml) and stirred at 21° for 2½ hours. The mixture was kept at 5° for 17 hours, diluted with ether (50 ml) and filtered. The solid was washed with ether and dried in vacuo to give the title compound (1.96 g), $[\alpha]_D^{21}$ −35° (c 1.4, CHCl$_3$); $\lambda_{max}$ (ethanol) 308 nm, $E_{1\ cm}^{1\%}$ 143; $\lambda_{inf}$ 260 nm, $E_{1\ cm}^{1\%}$ 166.

(c) Diphenylmethyl (6R,7R)-7-[(Z)-2-(t-Butoxycarbonylmethoxyimino)-2-(tritylaminothiazol-4-yl)acetamido]-3-(1-methylpyridinium-4-ylthiomethyl)ceph-3-em-4-carboxylate halide A mixture of the product of stage (b) (0.32 g), powdered anhydrous potassium iodide (0.24 g) and acetone (2 ml) was stirred and cooled to −3°. Acetyl chloride (0.1 ml) was added, and the mixture was stirred at 0° for 1 hour and then added to a solution of sodium metabisulphite (0.12 g) in water (15 ml). The mixture was stirred at 21° for 15 minutes and then filtered. The solid was washed with water and ether and dried in vacuo at 45° for 1 hour to give the title compound (0.25 g), the spectroscopic and chromatographic properties of which resembled those of the product of Example 2(b). The title compound may be deprotected as described in Example 2(c) to yield (6R,7R)-7-[(Z)-2-(2-aminothiazol-4-yl)-2-(carboxymethoxyimino)acetamido]-3-(1-methylpyridinium-4-ylthiomethyl)ceph-3-em-4-carboxylate, bis hydrochloride salt.

EXAMPLE 5

(a) Diphenylmethyl (1S,6R,7R)-3-Bromomethyl-7-[(Z)-2-(t-butoxycarbonyl-methoxyimino)-2-(2-(2-tritylaminothiazol-4-yl)acetamido]ceph-3-em-4-carboxylate, 1-oxide A solution of 85% metachloroperbenzoic acid (0.23 g) in 1,2-dichloroethane (20 ml) was added to a stirred solution of the product of Example 2(a) (0.99 g) in 1,2-dichloroethane (30 ml) maintained at −10°. The solution was warmed to 20° over 1 hour. More metachloroperbenzoic acid (0.02 g) was added and the solution was stirred at 20° for ½ hour. The solution was washed once with aqueous sodium metabisulphite solution and evaporated. The residue was combined with an ethyl acetate extract of the aqueous phase, washed with fresh sodium metabisulphite solution, sodium bicarbonate solution, and brine, and dried over sodium sulphate. The solution was evaporated and the residue was eluted through a column of Kieselgel 60 silica (ca 60 g) in ethyl acetate: petroleum ether (60°–80°) (1:1). Appropriate fractions were collected, combined, and evaporated to give a foam, which was triturated with diisopropyl ether. The solid was collected by filtration and dried in vacuo at 50° to give the title compound (0.5 g), $[\alpha]_D^{21}$ −2.2° (c 0.9, CHCl$_3$); $\lambda_{max.}$ (ethanol) 267.5 nm, $E_{1\ cm}^{1\%}$ 169; $\lambda_{inf.}$ 238 nm, $E_{1\ cm}^{1\%}$ 221; $\lambda_{inf.}$ 272.5 nm, $E_{1\ cm}^{1\%}$ 166.

(b) Diphenylmethyl (1S,6R,7R)-7-[(Z)-2-(t-Butoxycarbonylmethoxyimino)-2-(2-tritylaminothiazol-4-yl)acetamido]-3-(pyrid-4-ylthiomethyl)-ceph-3-em-4-carboxylate, 1-oxide A mixture of the product of stage 4 (a) (0.36 g), finely divided calcium carbonate (Calofort U, 0.12 g) and 4-mercaptopyridine (0.06 g) in acetone (12 ml) was stirred and refluxed for 90 minutes. The mixture was cooled and filtered. The residue was washed with a little acetone. The filtrate and washings were evaporated to a foam which was partitioned between ethyl acetate and water. The aqueous phase was extracted with ethyl acetate. The combined extracts were washed with water and brine, dried, and evaporated to a foam. This material was chromatographed on silica gel using chloroform containing ethanol (2%) and added methanol (0%–5%) as eluent. The appropriate fractions were combined and evaporated to give the title compound (0.12 g), $[\alpha]_D^{21}$ −2° (c 0.76, chloroform); $\lambda_{max.}$ (ethanol) 255 nm, $E_{1\ cm}^{1\%}$ 251; $\lambda_{inf.}$ 265 nm, $E_{1\ cm}^{1\%}$ 245; $\lambda_{inf.}$ 272.5 nm, $E_{1\ cm}^{1\%}$ 232.

(c) Diphenylmethyl (1S,6R,7R)-7-[(Z)-2-(t-Butoxycarbonylmethoxyimino)-2-(2-tritylaminothiazol-4-yl)acetamido]-3-(1-methylpyridinium-4-ylthiomethyl)ceph-3-em-4-carboxylate iodide, 1-oxide A solution of the product of stage (b) (55 mg) in iodomethane (0.5 ml) was allowed to stand at 21° for 2 hours. The solution was evaporated and the residue was triturated with ether. The solid was collected by filtration, washed with a little ether, and dried in vacuo at 50° for 1 hour to give the title compound, (43 mg), the spectroscopic and chromatographic properties of which resembled those of the product of Example 4(b). The title compound may deprotected as described in Example 2(c) to yield (6R,7R)-7-[(Z)-2-(2-aminothiazol-4-yl)-2-(carboxymethoxyimino)acetamido]-3-(1-methylpyridinium-4-ylthiomethyl)ceph-3-em-4-carboxylate, bis hydrochloride salt.

EXAMPLE 6

(1S,6R,7R)-7-[(Z)-2-(2-Aminothiazol-4-yl)-2-(carboxymethoxyimino)acetamido]-3-(1-methylpyridinium-4-ylthiomethyl)ceph-3-em-4-carboxylate, 1-oxide, dihydrochloride salt The Product of Example 4(b) (1.13 g) was stirred with anisole (4 ml) and trifluoroacetic acid (15 ml) at 0° for one hour. The mixture was evaporated and the residual oil was triturated with ether. The precipitate was collected by filtration and washed with ether to give a solid (0.8 g). This solid was dissolved in formic acid (4 ml) and concentrated hydrochloric acid (0.2 ml) was added. The mixture was stirred at 21° for 30 minutes and filtered. The filter cake was leached with formic acid and the combined filtrates were evaporated. The residue was triturated with acetone to give the title compound (535 mg), $[\alpha]_D^{22}$ −8° (c 0.83, pH7 buffer; $\lambda$max (pH6 buffer) 230.5 nm ($E_{1\ cm}^{1\%}$ 323), 258 nm ($E_{1\ cm}^{1\%}$ 242), 303.5 nm ($E_{1\ cm}^{1\%}$ 372).

PHARMACEUTICAL FORMULATIONS

The antibiotic compounds of the invention may be formulated for adminstration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers, if necessary with an added preservative. The compositions may also take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

If desired, such powder formulations may contain an appropriate non-toxic base in order to improve the water-solubility of the active ingredient and/or to ensure that when the powder is constituted with water, the pH of the resulting aqueous formulation is physiologically acceptable. Alternatively, the base may be present in the water with which the powder is constituted. The base may be, for example, an inorganic base.

The following formulations illustrate how the compounds according to the invention may be made up into pharmaceutical compositions.

A Formulation-For injection

Formula per Vial (6R,7R)-7-[(Z)-2-(2-Aminothiazol-4-yl)-2-(carboxymethoxyimino)acetamido]-3-(1-methylpyridinium-4-ylthiomethyl)ceph-3-em-4-carboxylate: 1.00 g
Sodium Carbonate, anhydrous: 112 mg

Method

Blend the sterile cephalosporin antibiotic with sterile sodium carbonate under aseptic conditions. Fill aseptically into glass vials under a blanket of sterile nitrogen.

Close the vials using rubber discs, or plugs, held in position by aluminium overseals, thereby preventing gaseous exchange or ingress of microorganisms. Constitute the product by dissolving in Water for Injections or other suitable sterile vehicle shortly before administration.

B Formulation for Injection

Fill sterile (6R,7R)-7-[(Z)-2-(2-aminothiazol-4-yl)-2-(carboxymethoxyimino)acetamido]-3-(1-methylpyridinium-4-ylthiomethyl)ceph-3-em-4-carboxylate monosodium salt into glass vials, such that each vial contains an amount equivalent to 500 mg of the antibiotic acid. Carry out the filling aseptically under a blanket of sterile nitrogen. Close the vials using rubber discs, or plugs, held in position by aluminium overseals, thereby preventing gaseous exchange or ingress of microorganisms. Constitute the product by dissolving in Water for Injections or other suitable sterile vehicle shortly before administration.

We claim:

1. A cephalosporin antibiotic of formula (wherein $Y^{\oplus}$ represents a C-attached 1-$C_{1-4}$ alkylpyridinium group) and non-toxic salts, non toxic metabolically labile esters and 1-oxides thereof.

2. A compound as claimed in claim 1 wherein $Y^{\oplus}$ represents a C-attached 1-methylpyridinium group.

3. A compound as claimed in claim 1 wherein $Y^{\oplus}$ represents a 1-$C_{1-4}$ alkylpyridinium group attached to the adjacent sulphur atom at the 2- or 4-position of the pyridine ring.

4. A compound as claimed in claim 1, said compound being (6R,7R)-7-[(Z)-2-(2-aminothiazol-4-yl)-2-carboxymethoxyimino)acetamido]-3-(1-methylpyridinium-2-ylthiomethyl)ceph-3-em-4-carboxylate.

5. A non-toxic salt of the compound of claim 4.

6. A compound as claimed in claim 1, said compound being (6R,7R)-7-[(Z)-2-(2-aminothiazol-4-yl)-2-(carboxymethoxyimino)acetamido]-3-(1-methylpyridinium-4-yl-thiomethyl)ceph-3-em-4-carboxylate.

7. A non-toxic salt of the compound of claim 6.

8. A compound as claimed in claim 1, said compound being (1S,6R,7R)-7-[(Z)-2-(2-aminothiazol-4-yl)-2-(carboxymethoxyimino)acetamido]-3-(1-methylpyridinium-4-ylthiomethyl)ceph-3-em-4-carboxylate, 1-oxide and its non-toxic salts.

9. A pharmaceutical composition for use in human or veterinary medicine comprising an effective amount of at least one antibiotic compound of claim 1 in association with a pharmaceutical carrier or excipient.

10. A method of combatting a bacterial infection in a human or a warm blooded animal comprising administering an antibacterially effective amount of at least one compound of claim 1.

* * * * *